(12) United States Patent
Lima Rocha et al.

(10) Patent No.: US 9,750,247 B2
(45) Date of Patent: Sep. 5, 2017

(54) NEMATOTOXIC COMPOSITION OF SYNERGISTIC EFFECT, USE OF A NEMATOTOXIC COMPOSITION OF SYNERGISTIC EFFECT

(71) Applicants: EMPRESA BRASILEIRA DE PESQUISA AGROPECUARIA—EMBRAPA, Brasilia-DF (BR); THE UNIVERSITY OF MELBOURNE, Victoria (AU)

(72) Inventors: Thales Lima Rocha, Brasilia (BR); Raphael Garcia de Sousa Evaristo, Brasilia (BR); Maria Fátima Grossi de Sá, Brasilia (BR); Djair dos Santos de Lima e Souza, Natal (BR); Maria Cristina Mattar da Silva, Brasilia (BR); Vera Lúcia Perussi Polez, Brasilia (BR); Ute Roessner, Victoria (AU); Tony Bacic, Victoria (AU)

(73) Assignees: EMPRESA BRASILEIRA DE PESQUISA AGROPECUARIA-EMBRAPA, Brasilia-DF (BR); UNITVERSITY OF MELBOURNE, Victoria (AU)

( * ) Notice: Subject to any disclaimer, the term of this patent is extended or adjusted under 35 U.S.C. 154(b) by 0 days.

(21) Appl. No.: 14/654,017

(22) PCT Filed: Dec. 26, 2013

(86) PCT No.: PCT/BR2013/000598
§ 371 (c)(1),
(2) Date: Jun. 19, 2015

(87) PCT Pub. No.: WO2014/100874
PCT Pub. Date: Jul. 3, 2014

(65) Prior Publication Data
US 2015/0313220 A1  Nov. 5, 2015

(30) Foreign Application Priority Data
Dec. 26, 2012  (BR) .......................... 1020120331462

(51) Int. Cl.
| *A01N 37/44* | (2006.01) |
| *A01N 37/00* | (2006.01) |
| *A01N 37/02* | (2006.01) |
| *A61K 31/19* | (2006.01) |
| *A61K 31/194* | (2006.01) |
| *A61K 31/195* | (2006.01) |
| *A01N 41/12* | (2006.01) |
| *A01N 37/06* | (2006.01) |
| *A01N 43/16* | (2006.01) |

(52) U.S. Cl.
CPC ............. *A01N 41/12* (2013.01); *A01N 37/02* (2013.01); *A01N 37/06* (2013.01); *A01N 43/16* (2013.01)

(58) Field of Classification Search
None
See application file for complete search history.

(56) References Cited

U.S. PATENT DOCUMENTS 9,055,745 B2 * 6/2015 James-Meyer ........ A01N 37/02

* cited by examiner

Primary Examiner — Alton Pryor
(74) Attorney, Agent, or Firm — Sughrue Mion, PLLC (57) ABSTRACT

The present invention relates generically to compositions used for controlling agricultural pests and, in a particular embodiment, to compositions usable for combating nematodes.

The invention presents a feasible alternative to the use of nematotoxic compounds that are harmful to the environment and that may damage human health. This alternative is embodied through a nematotoxic composition for controlling nematodes and that may be used on plants, parts of plants and on the soil. The respective technology results from unexpected results achieved from experiments carried out with extracts of the plant *Canavalia ensiformis*, resulting in an unheard-of nematotoxic composition comprising a specific combination of substances that are naturally found in the extract and that act synergistically.

33 Claims, 7 Drawing Sheets

NEMATOTOXIC COMPOSITION OF SYNERGISTIC EFFECT, USE OF A NEMATOTOXIC COMPOSITION OF SYNERGISTIC EFFECT

CROSS REFERENCE TO RELATED APPLICATIONS

This is a National Stage of International Application No. PCT/BR2013/000598 filed Dec. 26, 2013, claiming priority based on Brazilian Patent Application No. 10 2012 033146 2 filed Dec. 26, 2012, the contents of all of which are incorporated herein by reference in their entirety.

FIELD OF THE INVENTION

The present invention falls into the context of green chemistry and relates generically to compositions used for controlling agricultural pests and, in a particular embodiment, to compositions usable in combating nematodes.

DESCRIPTION OF THE PRIOR ART

Within the concept of sustainability, environmental chemistry and/or green chemistry has advanced toward introducing processes and products for replacement of polluting technologies. The use of raw-materials of vegetable origin and/or substances identical to those found in nature and the incorporation thereof into ecologically correct processes/products has proved to be a worldwide tendency, chiefly in countries that have great availability of biomass.

In Brazil, gall-nematodes (*Meloidogyne javanica* nematodes) figure among the most harmful pests in intensive agricultural areas for important crops, such as coffee beans, sugar-cane, soybeans, beans, tobacco, fruit trees and olericultural plants. The damages caused by these phytopathogens include formation of galls that cause unbalance in the absorption of water and nutrients from the soil, making the plants much more sensitive to any environmental modification or to the attack by pests and pathogens. Nematodes of the genus *Meloydogyne* spp are sedentary endoparasites compulsory on various plants. The hosts comprise over 3,000 vegetable species. Annual losses related to the action of these organisms approach US$ 150 billion, of which 90% are associated to the *Meloigogyne incognica, M. Javanica, M. arenaria* and *M. hapla* nematodes (Abad, et al, 2008; Bakhetia et al, 2005). In this context, *M incognita* nematode stands out as the most expressive species as to economic losses (Huang et al, 2006).

The strategies used for controlling this phytoparasite consists of: rotation of crops, use of resistant varieties, integrated handling of pests and chiefly application of synthetic agricultural defensives (Chitwood, 2002). The use of antagonist plants in rotation-of-crops schemes is one alternative, but with reduction in the productivity and in the profits of the farmer (Dufour et al, 2003; Ferraz & Freitas, 2000). The use of resistant varieties is a recommendable way of controlling pests and diseases, but the number of resistant cultivars is limited, as well as the genetic diversity related to this resistance (Dofour et all, 2003); Ferraz & Freitas, 2000). The integrated handling of pests is a desired strategy, but it needs strict planning, intensive management of the crop, higher expenditure of time and may have costs higher than the use of agricultural defensives (Gentz, 2010). The most widely used control strategy lies in the massive use of synthetic nematicides, which result in impairing the natural environment and public health (Abad et al, 2008). In this regard, the employ natural nematotoxic vegetable compounds (Newman et al, 2003) is a strategy for controlling this phytonemadode.

Significant advances in the metabolomics area of plants, and the integration thereof with genomics, transcriptomics, proteomics and bioinformatics have provided new possibilities for exploiting and extending complex interactions ion biological systems ((Weckwerth, 2009; Shulaev, 2008; Weckwerth, 2008; Huang, et al., 2008; Roessner et al., 2006; Roessner et al., 2001). Studies on the action of extracts obtained from seeds of antagonistic plants demonstrated quite effective nematicidal and nematostatic effects. These effects have been related to the presence of secondary metabolites, such as alkaloids, terpenes, tannins, flavonoids and glycosides (Chitood, 2002; Ferraz & Freitas, 2000).

Thus, it is of extreme importance to look for innovative natural chemical substances that have wide structural and biological diversity (Newman et al, 2003; Kirkpatrick, 2002), with a view to obtain new effective and environmental safe nematotoxic products. In this case, the plants are sources of over 100,000 natural products of small molecular mass, known as vegetable compounds or metabolites (Clardy, 2004; Dixon, 2001). In vegetables, these compounds may be associated to cellular differentiation, regulation of growth, measurement of interactions between plants and other organisms, and chiefly protection of the plant (Dobson, 2004).

Within this context, the present invention presents a feasible alternative to the use of namatotoxic compounds that are harmful to the environment and that may damage human health. This alternative is embodied through a nematotoxic composition for controlling nematodes that that can be used on plants, parts of plants and in the soil. The respective technology comes from unexpected results achieved from experiments carried out with extracts of *Canavalia ensiformis* plant, resulting in an unheard of nematotoxic composition comprising a specific combination of substances that are naturally found in the extract.

SUMMARY OF THE INVENTION

The present invention presents a composition comprising a specific combination of substances found naturally and that act synergistically on the control of nematodes on plants.

The synergistic nematotoxic composition of the present invention comprises, as active compounds:
- Trans-aconitic acid,
- Glucose, and optionally
- S-carboxymethylcysteine.

Among the forms of presentation of the present composition are solutions, emulsions, wettable powders, suspensions, powders, dusts, pastes, soluble powders, granules, suspension-emulsion concentrated, natural and synthetic materials impregnated with active compounds and mciroencapsulations in polymeric substances. Additionally, the composition of the invention may further comprise formulation ingredients, including, among others, liquid carriers/liquid solvents and/or solid carriers and/or surfactants and/or stickiness agents and/or dyes.

A second embodiment of the respective invention relates to the use of the synergistic nematotoxic composition for controlling nematodes on plants.

BRIEF DESCRIPTION OF THE FIGURES

FIG. 9—(A) Bioassay showing the effect of the commercial compounds on second-stage juveniles of *M. incognita* after 48 hours' exposure. 1—Control dH20, 2—DECE, 3—Glycose 10%, 4—Glycose 20%, 5—D-Pinitol (80 ug), 6—D-Pinitol (150 ug), 7—L-canavanina (80 ug), 8—L-canavanina (150 ug), 9—palmitic acid (80 ug), 10—palmitic acid (150 ug), 11—citric acid (80 ug), 12—citric acid (150 ug), 13—malic acid (80 ug), 14—malic acid (150 ug), 15—cis-aconitic acid (80 ug), 16—cis-anonitic acid (150 ug), 17—trans-anonitic acid (80 ug), 18—trans-aconitic acid (150 ug), 19—50 mM Tris/HCl pH 8, 20—50 mM acetic acid pH 5, 21—L-phenylamine (80 ug), 22—L-phenylamine (150 ug), 23—L-methionine (80 ug), 24—L-methionine (150 ug), 25—L-tryptophan (80 ug), 26—L-tryptophan (150 ug), 27—S-carboxymethylcistein (80 ug), 28—S-carboxymethylcisteine (150 ug), 29—Zantotoxine (80 ug), 30—Zantotoxine (150 ug), and 31—Glucose 20%+L-canavanine (15) ug). B—Evaluation of the effect of the different commercial compounds after the recovery assay using distilled water.

FIG. 10—(A) Bioassay showing the effect of the commercial compounds and their compositions on second-stage juveniles of *M. incognita* (J1) after 48 hours' exposure. C+ positive control (extract); C−: negative control (water); 2: palmitic acid; 3: S-carboxymethylcisteine; 4: trans-aconitic acid; 5: glucose. Concentrations of the compositions: 2+4, 2+4, 2+5, 3+4, 3+5=0, 25 g/L (each active compound of the composition); 2+3+4, 2+3+5, 2+4+5=0.17 g/L each active compound of the composition, 2+3+4+5=0.125 g/L each active compound of the composition. (B)—Evaluation of the effect of the different commercial compounds and their compositions after the recovery assay using distilled water. C+ positive control (extract); 2: palmitic acid; 3: S-carboxymethylcisteine; 4: trans-aconitic acid; 5: glucose. Concentrations of the compositions: 2+3, 2+4, 3+4, 3+5=0.25 g/L (each active compound of the composition); 2+3+4, 2+3+5, 2+4+5=0.17 g/L each active compound of the composition.

DETAILED DESCRIPTION OF THE INVENTION

The present invention is the result of research works carried out with a view to detect possible natural nematotoxic compounds present in plant extracts. Such compounds constitute an alternative in replacing nematotic synthetic agents that cause damages to nature and to man. The nematoxic composition described in the invention was generated unexpected results upon carrying out nematotoxicity bioassays using as active compounds a few substances detected in the plant extract. The results of these bioassays prove the existence of an unexpected synergistic nematotoxic effect.

In this context, the present invention describes a nematotoxic composition of synergistic effect comprising, as active compounds:

Trans-aconitic acid,
Glucose and optionally
S-carboxymethylcisteine.

The nematotoxic composition described in this invention may alternatively comprise formulation ingredients. Said composition, with or without the presence of formulation ingredients, may be in the form of solutions, emulsions, wettable powders, suspensions, powders, dusts, pastes, soluble powders, granules, suspension-emulsion concentrated, natural and synthetic materials impregnated with active compounds and mciroencapsulations in polymeric substances.

Among the compounds that can be used as formulation ingredients are, among others: liquid carriers/liquid solvents and/or solid carriers and/or surfactants and/or stickiness agents and/or dyes. If the formulation ingredient used is water, it is also possible to employ auxiliary solvents such as organic solvents.

Among liquid carriers/liquid solvents suitable for use in the present invention, one can cite, among others, aromatic solvents, chlorinated aromatic solvents or chlorinated aliphatic hydrocarbons, aliphatic hydrocarbons, petroleum fractions, mineral oils, vegetable oils, alcohols and their ethers and esters, ketones, strongly polar solvents and water.

Preferably, the aromatic solvents used in the invention are selected from xylene, toluene or alkyl naphtalenes. In the case of the use of chlorinated aromatic solvents or chlorinated aliphatic hydrocarbons in the composition of the present invention, these are preferably selected from chlorobenzene, chloroethylene or dichloromethane. Aliphatic hydrocarbons are preferably selected from cyclohexane or paraffins. In the alternative case of using alcohols, these are preferably selected from ethanol, propanol butanol or glycol. For the case of using ketones, these are preferably selected from propanone, methyl ethyl ketone, methyl isobutyl ketone or cyclohexanone. Strongly polar solvents are preferably selected from dimethylformamide and dimethyl sulfoxide.

Among the solid carriers suitable for use in the present invention, one can cite, among others, ammonium salts, ground natural minerals and ground synthetic minerals.

Preferably, when ground natural minerals are used as solid carriers, they are selected from kaolin, clays, talc, chalk, quartz, atapulgite, montmorilonite and diatomaceous earths. When using ground synthetic minerals, these are preferably selected from silica, alumina and silicates. Solid carriers suitable are used when the nematotoxic composition of the present invention is presented in the form of granules. These suitable solid carriers are preferably selected from ground natural rocks, synthetic granules and organic material granules.

Alternatively, surfactants may be employed as formulation ingredients for the composition of the present invention. The respective surfactants are selected from emulsifiers and/or dispersants and/or foam builders. Different emulsifiers/foam builders may be used in the nematotoxic composition of the present invention, including cationic, non-ionic and anionic emulsifiers. When using non-ionic and anionic emulsifiers, these are preferably selected from fatty polyoxyethylene esters, fatty polyoxyethylene ethers, alkyl sulfonates, alkyl sulfates, aryl sulfonates, and protein hydrolysates. In the case of using dispersants such as surfactants in the present invention, these are preferably selected from methylcellulose and lignin sulfite waste.

Other formulation ingredients may also, alternatively, be employed in the composition of the present invention. These ingredients include, among others, stickiness agents such as carboxymethylcellulose and natural and synthetic polymers in the form of powders, granules or latex, such as gum Arabic, polyvinyl alcohol and polyvinyl acetate. Other ingredients that may also be employed as formulation ingredients are mineral and vegetable oils, natural phospholipids such as cephalins lecithins, and synthetic phospholipids.

Alternatively, the nematotoxic composition of the present invention may also contain, as formulation ingredients, dyes such as inorganic pigments, such as iron oxide, titanium oxide and Prussia blue, and organic dyes such as alizarin dyes, azo dyes and metallic phthalocyanine dyes.

In an alternative embodiment of the present invention, the nematotoxic composition of synergistic effect may further comprise other active compounds. These other active compounds, when used, are selected from insecticides, attractors, sterilizing agents, bactericides, acaricides, fungicides, growth regulating substances, herbicides and safeners.

In another alternative embodiment of the present invention, the synergistic nematotoxic composition is an aqueous composition comprising the active compounds. In a preferred particular composition of the present invention, the nematotoxic composition is an aqueous composition containing palmitic acid and trans-aconitic acid in concentration of 0.25 g/L each. In a second preferred particular composition of the present invention, the nematotoxic composition is an aqueous composition containing palmitic acid and glucose in concentration of 0.25 g/L each. In a third preferred particular composition of the present invention, the nematotoxic composition is an aqueous composition containing palmitic acid, tans-aconitic acid and glucose ion concentration of 0.17 g/L. In a fourth preferred particular composition of the present invention, the nematotoxic composition is an aqueous composition containing palmitic acid, trans-aconic acid and S-carboxymethylcisteine in concentration of 0.17 g/L each. In a fifth preferred particular composition of the present invention, the nematotoxic composition is an aqueous composition containing palmitic acid, glucose and S-carboxymethylcisteine ion concentration of 0.17 g/L each. In a sixth preferred embodiment of the present invention, the nematotoxic composition is an aqueouos composition containing palmitic acid, glucose, S-carboxymethylcistein and trans-aconitic acid in concentration of 0.125 g/L each.

Another object of the present invention is the use of the nematotoxic composition of synergistic effect described before for controlling nematodes on plants. Particularly, said use takes place by applying the composition of the invention to the plant and/or parts thereof and/or to the soil.

The application of the synergistic nematotoxic composition of the present invention to the plant and/or parts thereof and/or the soil may be carried out either directly or by allowing the compounds to act on their vicinities, environment or storage space by the ordinary treatment methods, for example, by immersion, spraying, evaporation, mist, spreading, etc.

In a special embodiment of the present invention, the use of the nematotoxic composition of synergistic effect described in this document is for controlling *Meloigonyne incognita*.

Experiments Carried Out and Results Achieved

Initially, aqueous extracts obtained from seeds of antagonistic plants were tested in bioassays with a view to detect compounds effective against second-stage juveniles (J2) of *M. incognita*.

Figure 1:
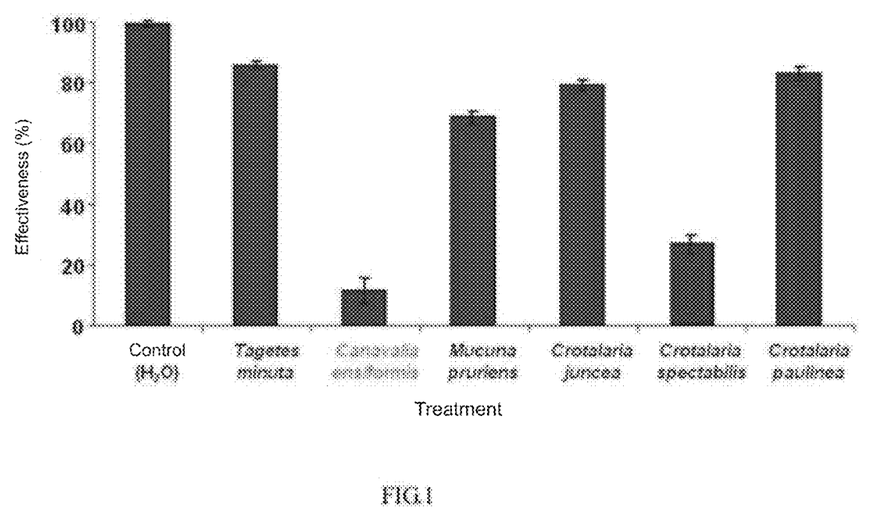
FIG. 1—effect of the aqueous crude extracts of seeds of antagonistic plants on (J2) of *M. incognita*. The bars represent the percentage of live nematodes after 48 hours' exposure. Concentration of 1 mg of each extract for a final volume of 0.3 mL and 100 second-stage juveniles was used in the bioassay in triplicate, having distilled water as negative control.
Figure 2:
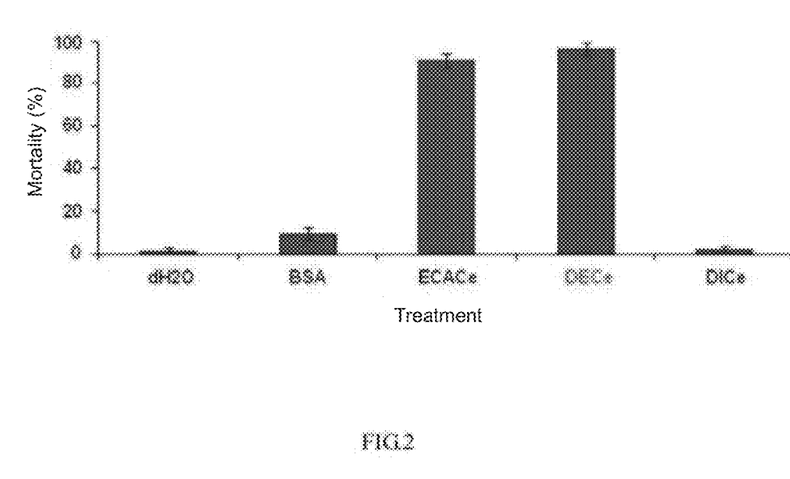
FIG. 2—Effect of 0.5 mg (0.5 mg/0.3 ml final volume) of the external (DECE) and internal (DICE) dialysates on J2 of *M. incognita*. The bars represent the percentage of dead nematodes. Controls were carried with distilled water (dH2O), bovine serum albumin (BSA) and aqueous crude extract of *C. ensiformis* (ECACe). Recovery assay carried out for certification of the nematicidal effect.
Figure 3:
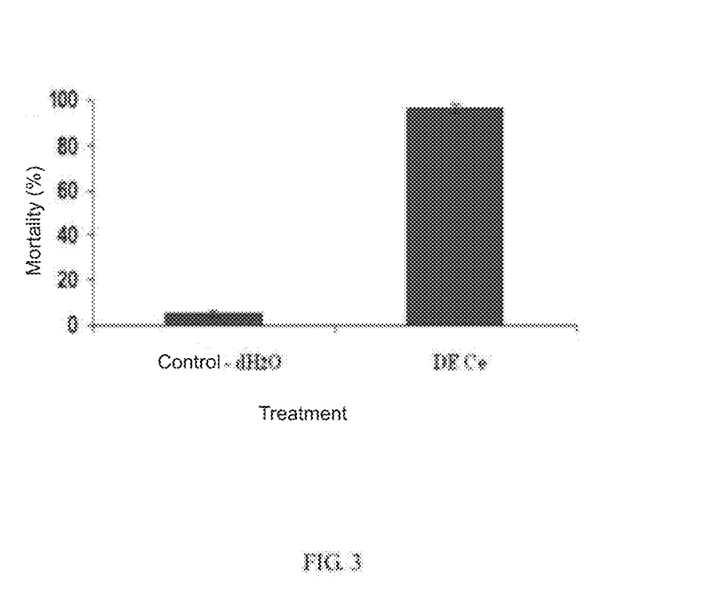
FIG. 3—Effect of the pre-heated (50° C.) DE of *C. ensiformis* versus J2 of *M. incognita*, demonstrating the thermal stability of the analyzed fraction. The bioassay was carried out in triplicate, and the bars represent the percentage of dead nematodes. Distilled water was used as negative control. Recovery assay carried out for certification of the nematicidal effect.
Figure 4:
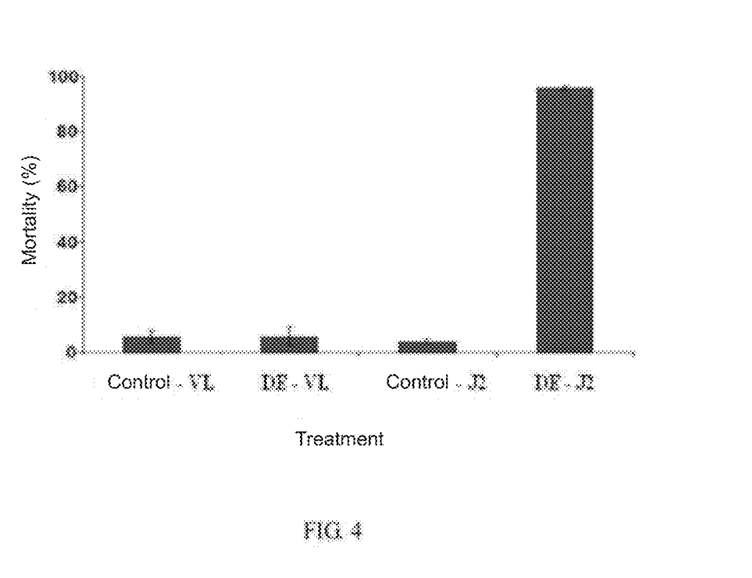
FIG. 4—Effect of 500 μg/0.3 mL) of DE of *C. ensiformis* on saprophytic nematodes of free life (FL/VL) and J2 of *M. incocnita*. The bars represent the percentage of dead nematodes. The controls of the bioassay have nematodes (VL) and J2 of *M. incognita* immersed separately in distilled water.
Figure 5:
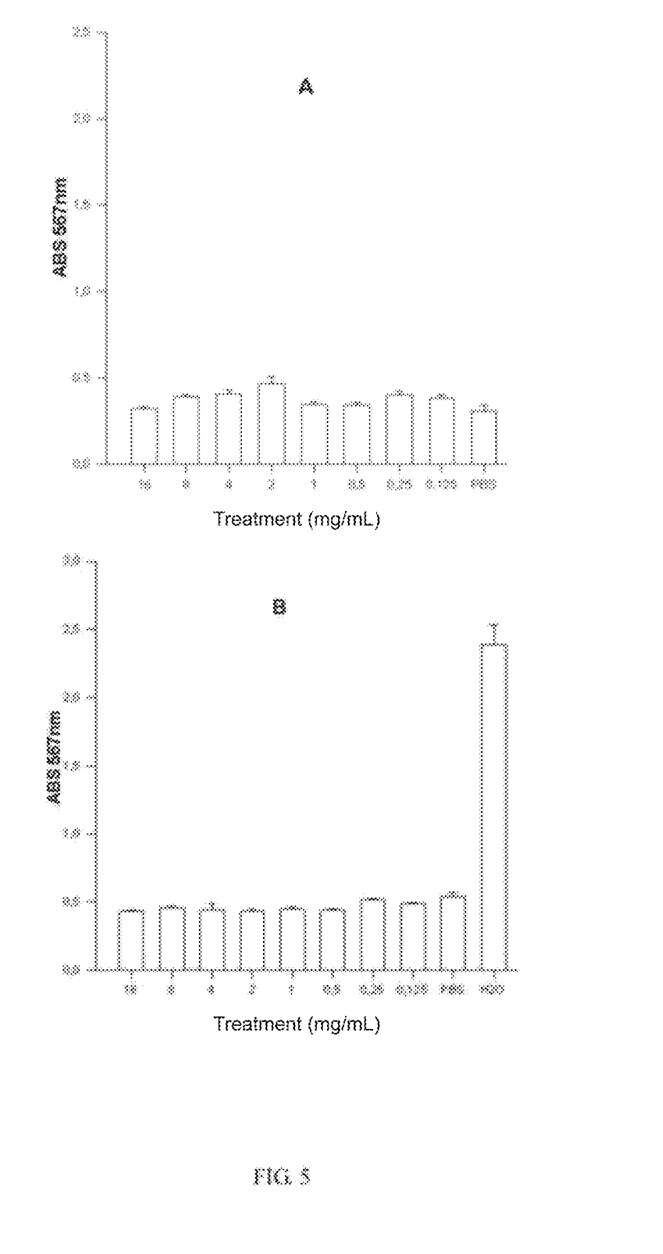
FIG. 5—Test of hemolytic activity using bovine blood (A) or purified erythrocytes (B) incubated with different concentrations of external dialysate of *C. ensiformis* sulublized in PBS. The measurements of hemolytic activity were monitored spectrophotometrically by using 567-nm wavelengths. Distilled water (100% hemolysis) and PBS were used as positive and negative controls.
Figure 6:
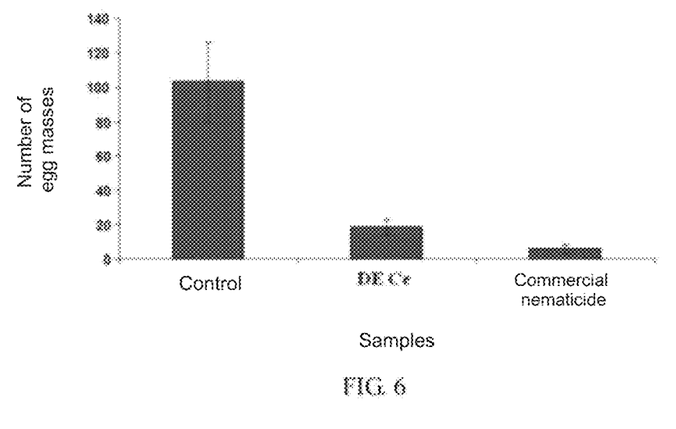
FIG. 6—Effect of the external dialysate (DE) of *C. ensiformis* on J2 of *M. incognita* in greenhouse simulating field conditions. The bars symbolize the number of egg masses found in the roots of tomato-plants after the treatments. The experiment was conducted in quintuplicate with distilled water and the commercial nematicide being used as negative and positive controls, respectively.

Among the extracts tested, *Canavalia ensiformis*, a plant of the family Leguminosae, originating in Central America, exhibited the highest nematicidal activity (85%) (FIG. 1). The fractioning of this material by dialysis resulted in the separation of molecules smaller than 3.5 kDa (external dialysate—DE) and bigger than 3.5 kDa (internal dialysate—DI). In this case, the DE exhibited the most promising results as compared to the DI, such as: a) higher nematotoxic activity (FIG. 20); b) thermal stability (FIG. 3); c) high specificity against J2 of *M. incognita* (Table 1); d) absence of activity against fungi (phitopathogenic *Collectotrichum gloeosporioides* access 1915, *Fusarium solani* access 1624, *Macrophomina phaseolina* access 1496 and *Phytophthora tabacum*), bacterium (*Bacillus subtilis*) and insect larva (*Antonomus grandis* and *Spodoptera frugiperda*) (Table 1); e) non-existence of activity against free-life nematode (FIG. 4); absence of adverse cytotoxic effect on red cells of mammals (FIG. 5) and g) reduction higher than 80% of the *M. incognita* egg masses in bioassays conducted in greenhouse by using tomato plants (FIG. 6).

Figure 7:
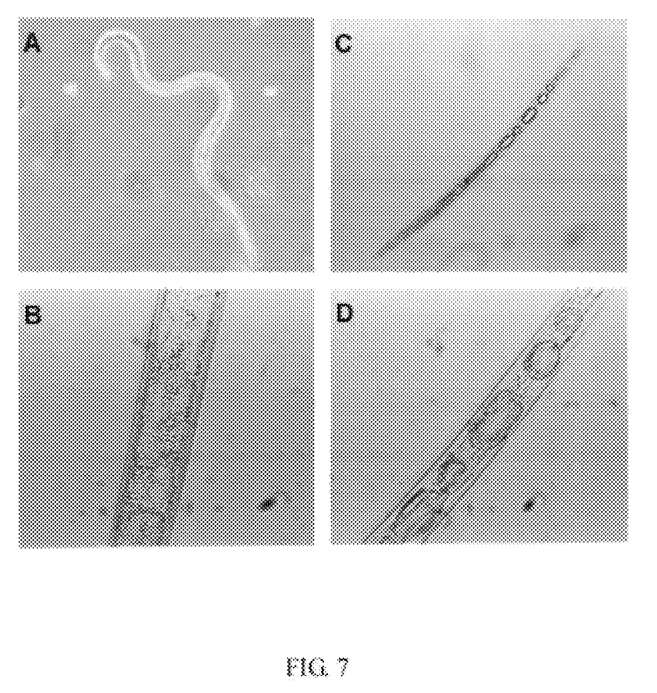
FIG. 7—Optical microscopy: (A) J2 before adding DE—200×. (B) Intestinal region of J2 before adding DE—400×. (C) J2 24 hours after adding DE—200×. (D) Intestinal region of J2 after adding DE—400×.

Additionally, the viewing by optical microscopy of the effect caused by the compound (s) present in the De of *C. ensiformis* on J2 of *M. incognita* disclosed the break of the normal anatomy (FIGS. 7—A, B, C and D) with formation of various vacuoles along the stiff body of the nematode. The alterations suggest the destructuring of tissues of the intestines of the phytoparasite.

TABLE I

Results achieved in the assays for specificity conducted in vitro by using different concentrations of DE of C. ensiformis against fungus, bacterium, insect larvae and nematode. The bioassays we3e carried out ion triplicate. A = Fungus, B = Bacterium, C = Larvae of insect and D = Nematode

| Pathogen | µg of DE of C. ensiformis/ Bioeassay | Activity |
| --- | --- | --- |
| A Colletotriclum gloeosporinoides | 250, 500, 1000 | Innocuous - complete absence of halo |
| A Fusarium solani | 250, 500, 1000 | Innocuous - complete absence of halo |
| A Macrophomina phaseoline | 250, 500, 1000 | Innocuous - complete absence of halo |
| B Bacillus subtilis | 250, 500, 1000 | Innocuous - complete absence of halo |
| A Anthonomus grandis (Larva) | 1000 | Innocuous - complete absence of halo |
| C Soidiotera frugiperda (Larva) | 1000 | Innocuous - complete absence of halo |
| D Dematoide saprofitico | 500 | Innocuous |
| D Dematoidogine incognita | 500 | Nematicidal |

Figure 8:
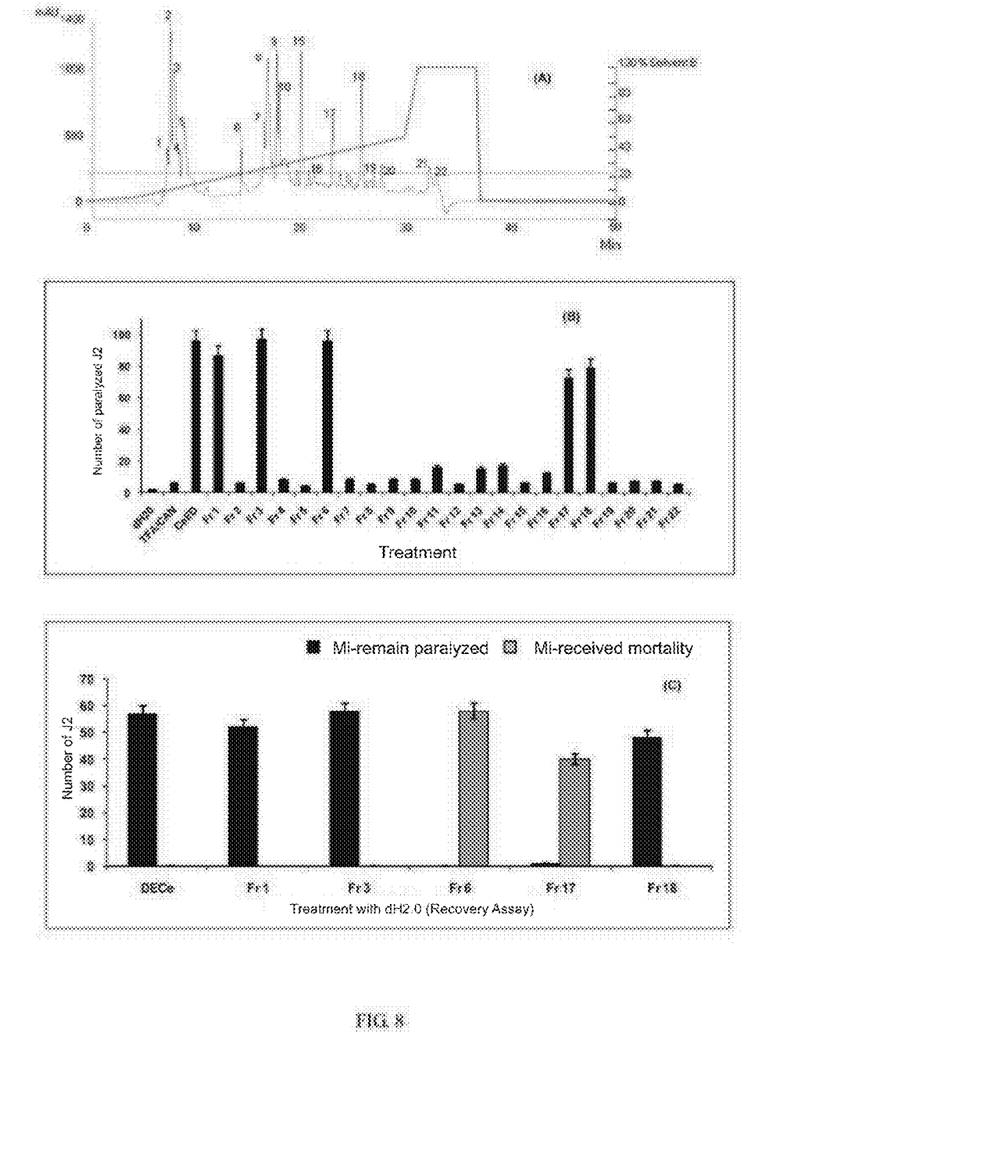
FIG. 8 (A) Chromatography of the external dialysate (DE) of *C. ensiformis* (λ=216 nm) exhibiting a profile with 22 peaks. (B)—Bioassay showing the active fractions against J2 of *M. incognita* (1, 3, 6, 17 and 18) after 48 hours' exposure. (C)—Recovery assay certifying the nematicidal effect of the fractions 1, 3 and 18 and nematostatic effect of fractions 6 and 17.

The purification of the DE via HPLC using reverse column phase (C18 enabled the separation of three nematicidal fractions and two nematostatic ones. All the steps were monitored by bioassays for evaluation of the nematotoxic activity (FIGS. 8 A, B and C). The active fractions were analyzed by Metabolite profiling by using the techniques of gaseous chromatography coupled to mass spectrometry (GC-MS), liquid chromatogeraphy coupled to mass spectrometry (LC-MS) and nuclear magnetic resonance (1H RMN). The data generated by these technologies added to a vast research in the literature enabled identification of nine compounds with nematotoxic action.

Figure 9:
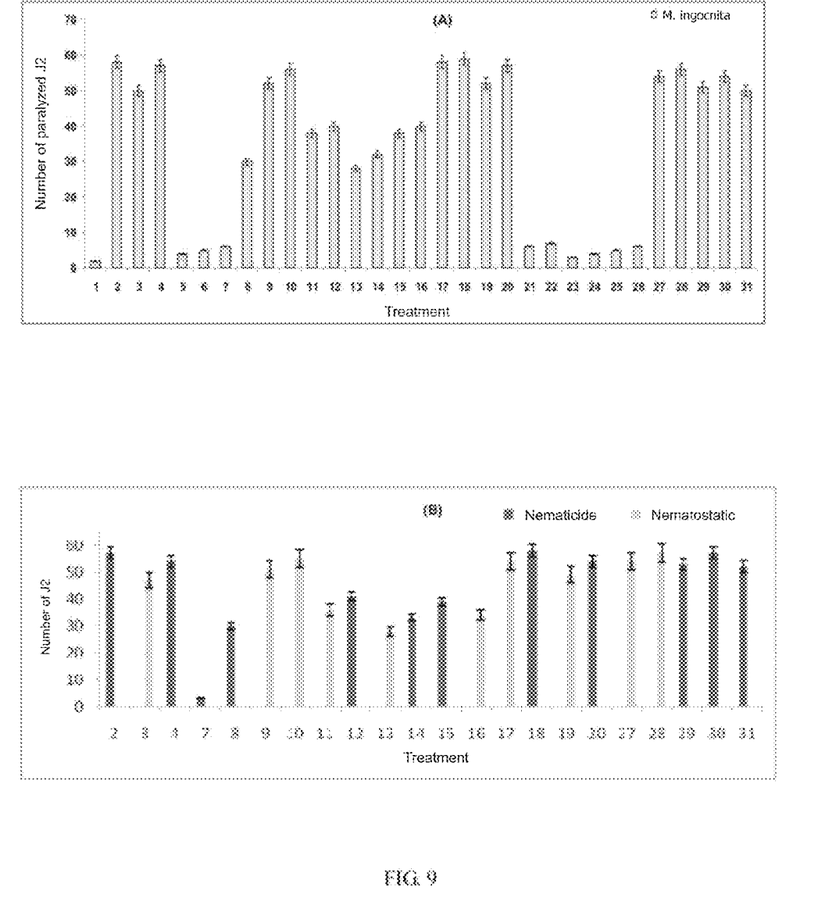

In this context, compounds produced commercially with biological functions identified after research in the literature and present in the nematotoxic fractions of C. ensiformis were tested in bioassay against M. incognita juveniles (FIG. 9A). Glucose solution containing 10% (W/V) was capable of paralyzing most of the nematodes after a period of exposure of 48 hours (FIG. 9A). After the recovery assay, 87% of the J2 reestablished the mobility, confirming the nematostatic activity for the concentration of applied glucose (FIG. 9A). However, glucose solutions containing 20% (W/V) exhibited a nematicidal effect killing over 90% of the J2 after 48 hours exposure (FIG. 9B). The vegetable carbohydrate D-pinitol did not exhibit any toxic effect after 48 hours' exposure against J2 of M. incognita, using concentrations of 80 µg/300 µL and 150 µg/300 µL, respectively (FIG. 9A). Similarly, the non-protein amino acid L-canavanine did not exhibit any nematotoxic activity for concentration of 80 µg/300 µL after 48 hours' exposure (FIG. 9A). However, when the concentration is increased to 105 µg/300 µL, 25% of the juveniles remained paralyzed after the recovery assay, thus confirming a modest nematicidal activity (FIG. 9B). Among the organic acids: malic, citric, cis-aconitic, trans-aconitic and palmitic, only the latter two acids were capable of paralyzing 90 and 98% of the J2 of M. incognita for concentration of 80 µg/300 µL after 48 hours' exposure (FIG. 9A). The other organic acids paralyzed a very low percentage of J2 for the same concentration and exposure time (FIG. 9A). For concentration of 150 µg/300 µL, the transaconitic acid exhibited nematicidal activity of 98%, while the malic, citric and cis-aconitic acids exhibited a nematicidal effect of only 18, 25 and 40% after the recovery assay (FIG. 9B). On the other hand, the palmitic acid demonstrated a nematostatic effect for both concentrations evaluated with 90% of the J2 recovering the mobility after the recovery test (FIG. 9B). These results show clearly a dose-dependent effect of the organic acids tested. The amino acids L-phenylamnine and L-triptofane were not capable of affecting the J2 using concentrations of 80 µg/300 µL and 150 µg/300 µL, respectively (FIG. 9A). Inversely, the compound S-carboxymethylcisteine paralyzed about 90% of the juveniles after 48 hours' exposure for both concentrations of 80 µg/300 µL and 150 µg/300 µL (FIG. 9A). Recovery assay confirmed the nematostatic effect with most J2 recovering the movement (FIG. 9B). Xantotoxin paralyzed 87% of the J2 after 48 hours' exposure for both the concentration of 80 µg/300 µL and the concentration 150 µg/300 µL (FIG. 9A). The J2 subjected to the recovery assay using both concentrations did not recover the mobility, confirming the nematicidal effect (FIG. 9B).

With a view to obtain a nematotoxic composition from the compounds with nematotoxic activity, detected in the prior experiments, the compounds glucose (5), trans-aconitic acid (4) and S-carboxymethylcisteine (3) and palmitic acid (2) were tested by carrying out in vitro experiments in different combinations. Although of xantotoxine demonstrates nematicidal action, it was not selected for aid tests due to the high cost and the difficulty of its chemical synthesis.

The compositions containing combinations of active compounds were tested by carrying out in vitro bioassays against M. incognita juveniles. The active compounds used in the experiments carried out were obtained commercially.

The compositions tested were:
a) Glucose+S-carboxymethylcisteine (0.25 g/L of each compound;
b) Glucose+palmitic acid (0.25 g/L of each compound);
c) S-carboxymethylcisteione+palmitic acid (0.25 g/L of each compound;
d) S-carboxymethylcisteine+trans-aconitic acid (0.25 g/L of each compound);
e) Palmitic acid+trans-aconitic acid (0.25 g/L of each compound);
f) Glucose+S-carboxymethylcisteine+palmitic acid (0.17 g/L of each compound);
g) Glucose+palmitic acid+trans-aconitic acid (0.17 g/L of each compound);
h) S-carbocxymethylcisteione+trans-aconitic acid+palmitic acid (0.17 g/L of each compound);
i) Glucose+S-carboxymethylcisteine+trans-aconitic acid+palmitic acid (0.125 g/L of each compound).

Figure 10:
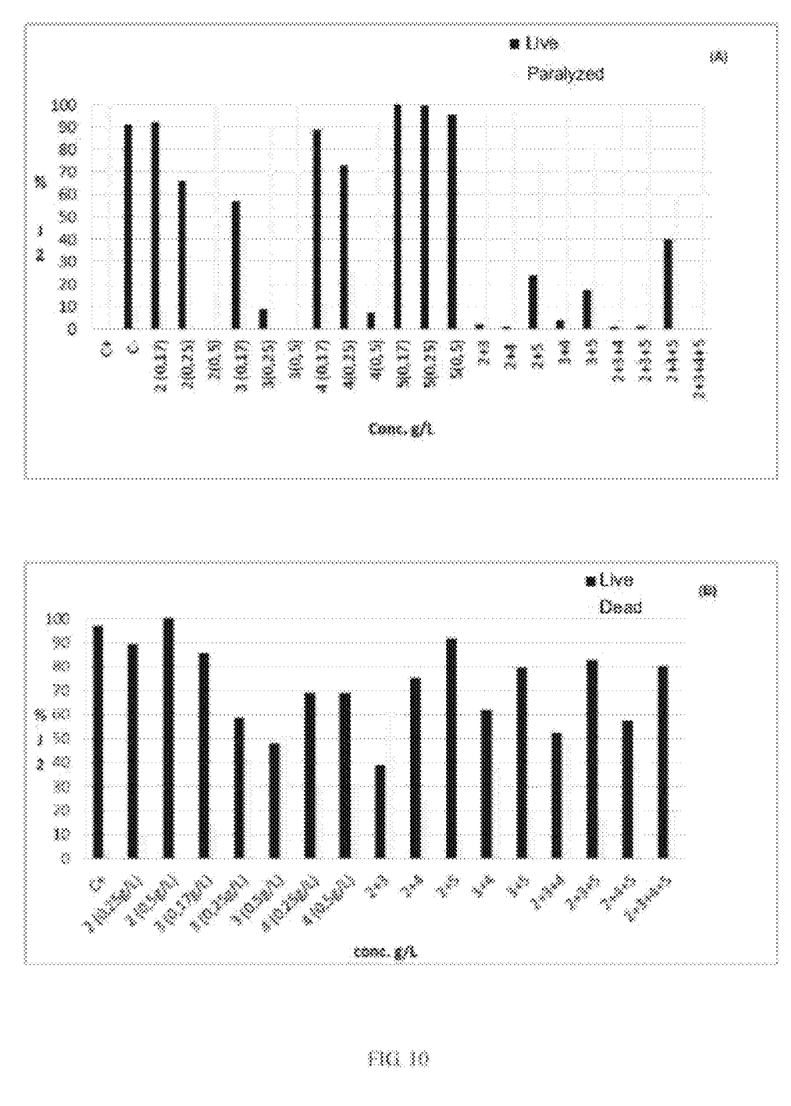

The results achieved through the tests carried out with the compositions a) do i), are shown in FIGS. 10 (A) and (B) and commented on hereinafter.

As can be seen in FIG. 10A, the compositions b)e),f),g)h) and i) exhibit a synergistic nematotoxic effect as with regard to the paralyzation of the nematodes, as compared to the sum of the results obtained individually by each active compound. Said comparisons are shown in Table 2 to 7 below.

TABLE 2

Synergistic nematotoxic effect obtained after tests with the composition b)

| Active compound or composition | Concentration (g/L) | % of paralyzed nematodes |
| --- | --- | --- |
| glucose | 0.25 | 0.71 |
| Palmitic acid | 0.25 | 33.86 |
| Glucose + palmitic composition | 0.25 (of each compound) | 76.27 |

The analysis of the results obtained in the recovery assays and shown in FIG. 10B indicates that the synergistic nematotoxic effect obtained by composition a) corresponded to a nematostatic effect.

TABLE 3

Synergistic nematotoxic effect obtained after tests with composition c)

| Active compound of composition | Concentration (g/L) | % paralyzed nematodes |
|---|---|---|
| Active compound or concentration (g/L) composition | | |
| Trans-aconitic acid | 0.25 | 27.08 |
| Palmitic acid | 0.25 | 33.86 |
| Trans-aconitic acid + palmitic acid composition | 0.25 (of each compound) | 99.05 |

The analysis of the results obtained in the recovery assays and shown in FIG. 10B indicates that the synergistic nematotoxic effect obtained by composition e) corresponded to a nematostatic effect.

TABLE 4

Synergistic nematotoxic effect obtained after tests with composition f.

| Active compound or composition | Concentration (g/L) | % paralyzed nematodes |
|---|---|---|
| Glucose | 0.17 | 0 |
| Palmitic acid | 0.17 | 7.66 |
| S-carboxymethylcisteine | 0.17 | 43.03 |
| Glucose + palmitic acid composition + S-carboxymethylcisteine compound | 0.17 (of each compound) | 98.61 |

The analysis of the results achieved in the recovery assays and shown in FIG. 10B show that the synergistic nematotoxic effect obtained after tests with composition f) was a nematostatic result.

TABLE 5

Synergistic nematotoxic effect obtained after tests with composition g)

| Active compound or composition | Concentration (g/L) | % Paralyzed nematodes |
|---|---|---|
| Glucose | 0.17 | 0 |
| Palmitic acid | 0.17 | 7.66 |
| Trans-aconitic acid | 0.17 | 11.12 |
| Glucose + palmitic acid + trans-aconit acid composition | 0.17 | 60.2 |

The analysis of the results obtained in the recovery assays and shown in FIG. 10B indicates that the synergistic nematotoxic effect obtained by composition g) was a nematostatic effect.

TABLE 6

Synergistic nematotoxic effect obtained after tests with composition h)

| Active compound or composition | Concentration (g/L) | % Paralyzed nematodes |
|---|---|---|
| S-carboxymethylcisteine | 0.17 | 43.03 |
| Palmitic acid | 0.17 | 7.66 |

TABLE 6-continued

Synergistic nematotoxic effect obtained after tests with composition h)

| Active compound or composition | Concentration (g/L) | % Paralyzed nematodes |
|---|---|---|
| Trans-aconitic acid | 0.17 | 11.12 |
| S-carboxymethylcisteine + palmitic acid composition + trans-aconitic acid composition | 0.17 (of each compound) | 99.32 |

The analysis of the results obtained in the recovery assays and shown in FIG. 10B indicates that the synergistic nematotoxic effect obtained by composition g) was a nematostatic effect.

TABLE 7

Synergistic nematodoxic effect obtained after tests with composition i.

| Active compound or composition | Concentration (g/L) | % paralyzed nematodes |
|---|---|---|
| S-carboxymethylcisteine | 0.125 | <43.03 |
| Glucose | 0.125 | 0 |
| Trans-aconitic acid | 0.125 | <11.12 |
| Palmitic acid | 0.125 | <7.66 |
| S-carboxymethylcisteine + palmitic acid + trans-aconitic acid + glucose composition | 0.125 (of each compound) | 100 |

The analysis of the results obtained in the recovery assays and shown in FIG. 10B indicates that the synergistic nematotoxic effect obtained by composition i) was a nematostatic effect.

The nematotoxic compositions a), c), d), the results of in vitro assays of which are also shown in FIGS. 10A and 10B, do not represent a significant synergistic nematotoxic effect.

The invention claimed is:

1. A nematotoxic composition comprising, as active compounds:
   Palmitic acid;
   Trans-aconitic acid and/or glucose and, optionally, S-carboxymethylcisteine,
   wherein a combination of the palmitic acid, Trans-aconitic acid and/or glucose, and optionally S-carboxymethylcisteine exhibits synergy.

2. The nematotoxic composition according to claim 1, further comprising one or more formulation ingredients.

3. The nematotoxic composition according to claim 1, wherein the nematoxic composition is in a form selected from the group consisting of a solution, an emulsion, a wettable powder, a suspension, a power, a dust, a paste, a soluble powder, granules, a suspension-emulsion concentrate, a natural and/or synthetic material impregnated with the active compounds, and a microencapsulation in a polymeric substance.

4. The nematotoxic composition according to claim 2, wherein the formulation ingredients are one or more liquid carriers/liquid solvents and/or one or more solid carriers and/or one or more surfactants and/or one or more stickiness agents and/or one or more dyes.

5. The nematotoxic composition according to claim 4, wherein the formulation ingredients are one or more liquid carriers/liquid solvents and the liquid carriers/liquid solvents are selected from the group consisting of aromatic solvents, chlorinated aromatic solvents or chlorinated aliphatic hydrocarbons, aliphatic hydrocarbons, petroleum fractions, mineral oils, vegetable oils, alcohols and their ethers and esters, ketones, strongly polar solvents and water.

6. The nematotoxic composition according to claim 5, wherein the liquid carriers/liquid solvents are aromatic solvents selected from xylene, toluene or alkylnaphthalenes.

7. The nematotoxic composition according to claim 5, wherein the liquid carriers/liquid solvents are chlorinated aromatic solvents or chlorinated aliphatic hydrocarbons selected from chlorobensene, chloroethylene or dichloromethane.

8. The nematotoxic composition according to claim 5, wherein the liquid carriers/liquid solvents are aliphatic hydrocarbons selected from cyclohexane or paraffins.

9. The nematotoxic composition according to claim 5, wherein the liquid carriers/liquid solvents are alcohols selected from ethanol, propanol, butanol or glycol.

10. The nematotoxic composition according to claim 5, wherein the liquid carriers/liquid solvent are ketones selected from propanone, methyl ethyl ketone, methyl isobutyl ketone or cyclohexanone.

11. The nematotoxic composition according to claim 5, wherein the liquid carriers/liquid solvents are strongly polar solvents selected from dimethylformamide or dimethyl sulfoxide.

12. The nematotoxic composition according to claim 4, wherein the solid carriers are selected from ammonium salts, ground natural minerals or ground synthetic minerals.

13. The nematotoxic composition according to claim 12, wherein the solid carriers are ground natural minerals selected from kaolin, clays, talc, chalk, quartz, atapulgite, montmorilonite or diatomaceous earth.

14. The nematotoxic composition according to claim 12, wherein the solid carriers are ground synthetic minerals selected from silica, alumina or silicates.

15. The nematotoxic composition according to claim 4, wherein the solid carriers are in the form of granules selected from ground natural rocks, synthetic granules or organic material granules.

16. The nematotoxic composition according to claim 4, wherein the formulation ingredients are one or more surfactants selected from emulsifiers and/or dispersants and/or foam builders.

17. The nematotoxic composition according to claim 16, wherein the formulation ingredients are the one or more emulsifiers selected from cationic, non-ionic or anionic emulsifiers.

18. The nematotoxic composition according to claim 17, wherein the one Of more emulsifiers are non-ionic and/or anionic emulsifiers selected from polyoxyethyele fatty esters, polyoxyethylene fatty ethers, alkyl sulfonates, alkyl sulfates, aryl sulfonates, and protein hydrolysates.

19. The nematotoxic composition according to claim 16, wherein the formulation ingredients are one or more dispersants selected from methylcellulose or lignin sulfite waste.

20. The nematotoxic composition according to claim 4, wherein the formulation ingredients are one or more stickiness agents selected from carboxymethylcellulose, natural polymers or synthetic polymers.

21. The nematotoxic composition according to claim 4, wherein the formulation ingredients are one or more dyes selected from inorganic pigments or organic dyes.

22. The nematotoxic composition according to claim 1, further comprising one or more additional active compounds.

23. The nematotoxic composition according to claim 22, wherein the one or more additional active compounds are selected from insecticides, attractors, sterilizing agents, bactericides, acaricides, namaticides, fungicides, growth-regulating substances, herbicides or safeners.

24. The nematotoxic composition according to claim 1, wherein the composition is an aqueous composition.

25. The nematotoxic composition according to claim 24, wherein the aqueous composition contains palmitic acid and trans-aconitic acid in a concentration of 0.25 g/L each.

26. The nematotoxic composition according to claim 24, wherein the aqueous composition contains palmitic acid and glucose in a concentration of 0.17 g/L each.

27. The nematotoxic composition according to claim 24, wherein the aqueous composition contains palmitic acid, trans-aconitic acid and glucose in a concentration of 0.17 g/L each.

28. The nematotoxic composition according to claim 24, wherein the aqueous composition contains palmitic acid, trans-aconitic acid and S-carboxymethylcisteine in a concentration of 0.17 g/L each.

29. The nematotoxic composition according to claim 24, wherein the aqueous composition contains palmitic acid, glucose and S-carboxymethylcisteine in a concentration of 0.17 g/L each.

30. The nematotoxic composition according to claim 24, wherein the aqueous composition contains palmitic acid, trans-aconitic acid, glucose and S-carboxymethylcisteine in a concentration of 0.25 g/L each.

31. A method for controlling nematodes on a plant, comprising:
    applying the nematotoxic composition according to claim 1 to the plant and/or to parts of the plant and/or to the soil to control nematodes on the plant.

32. The method according to claim 31, wherein the nematoxic composition is applied to the plant.

33. The method according to claim 31, wherein the nematodes are *Meloidogyne incognita*.

\* \* \* \* \*